(12) United States Patent
Shigeura (10) Patent No.: US 7,485,085 B2
(45) Date of Patent: Feb. 3, 2009

(54) HEAT TRANSFER FOR THERMAL CYCLING

(75) Inventor: John Shigeura, Portola Valley, CA (US);
Janice G. Shigeura, legal representative, Portola Valley, CA (US)

(73) Assignee: Applied Biosystems Inc., Foster City, CA (US)

( * ) Notice: Subject to any disclaimer, the term of this patent is extended or adjusted under 35 U.S.C. 154(b) by 1101 days.

(21) Appl. No.: 10/763,537

(22) Filed: Jan. 23, 2004

(65) Prior Publication Data

US 2005/0161192 A1    Jul. 28, 2005

(51) Int. Cl.
*B04B 15/02*    (2006.01)
*C12P 19/34*    (2006.01)

(52) U.S. Cl. .................. 494/14; 435/91.2

(58) Field of Classification Search .......... 494/14, 494/16, 20, 60; 435/91.2, 286.1, 186.6, 303.1; 219/400, 635; 369/275.1, 275.3; 432/180–181; 422/68.1
See application file for complete search history.

(56) References Cited

U.S. PATENT DOCUMENTS

| | | | |
|---|---|---|---|
| 3,616,264 | A | 10/1971 | Ray |
| 4,420,679 | A | 12/1983 | Howe |
| 5,455,175 | A | 10/1995 | Wittwer |
| 5,490,830 | A | 2/1996 | Lovelady et al. |
| 5,628,629 | A * | 5/1997 | Mitani et al. .......... 432/180 |
| 5,772,572 | A | 6/1998 | Koch et al. |
| 5,783,439 | A | 7/1998 | Reichler |
| 6,030,581 | A | 2/2000 | Virtanen |
| 6,482,615 | B2 | 9/2002 | Tal |
| 2002/0047003 | A1 | 4/2002 | Bedingham et al. |

FOREIGN PATENT DOCUMENTS

WO    WO 98/38510 A2    9/1998

OTHER PUBLICATIONS

International Search Report for Int'l Application No. PCT/US2005/001604 dated Jun. 16, 2005; along with Written Opinion of the ISA.

* cited by examiner

*Primary Examiner*—Saeid Ebrahimi Dehkordy (57) ABSTRACT

The present application relates to an apparatus and method for heat transfer for thermal cycling.

12 Claims, 13 Drawing Sheets

FIG. 12

HEAT TRANSFER FOR THERMAL CYCLING

FIELD

The present application relates to an apparatus and method for heat transfer for thermal cycling.

INTRODUCTION

Thermal cycling of biological reactions can utilize different types of heat transfer. Heat transfer for thermal cycling can include conduction, radiation, and/or convection to transfer heat to one or more sample chambers and to control the temperature during thermal cycling.

Examples of reactions of biological samples include polymerase chain reaction (PCR) and other reactions such as ligase chain reaction, antibody binding reaction, oligonucleotide ligation assays, and hybridization assays. In PCR, biological samples can be thermally cycled through a temperature-time protocol that includes denaturing DNA into single strands, annealing primers to the single strands, and extending those primers to make new copies of double-stranded DNA. During thermal cycling, in certain instances, it is desirable to maintain thermal uniformity throughout the sample chambers so that different samples can be heated and cooled uniformly to obtain uniform sample yields. Uniform yields can provide quantification between sample wells.

SUMMARY

According to various embodiments, a device for thermally cycling a sample comprises at least one heating element; a disc configured to receive samples; and a mechanism configured to rotate the disc, wherein rotation of the disc induces a turbulent airflow between at least a portion of the disc and at least a portion of the heating element.

According to various embodiments, a device for thermally cycling a sample, comprises: at least one heating element; a disc configured to receive samples; an air gap between at least a portion of the disc and at least a portion of the heating element; and a mechanism configured to rotate the disc, wherein rotation of the disc induces a turbulent airflow within the air gap.

According to various embodiments, a device for thermally cycling a sample comprises at least one heating element; a first mechanism configured to receive a disc wherein the disc is configured to receive samples; an air gap between the disc and the heating element when the disc is included in the first mechanism; and a second mechanism configured to rotate the disc, wherein rotation of the disc induces a turbulent airflow within the air gap.

According to various embodiments, a method of thermally cycling comprises at least one of introducing and removing heat with a heating element; and rotating a disc to induce a turbulent airflow, wherein the disc is configured to receive samples; and wherein there is an air gap between the disc and the heating element.

DESCRIPTION OF VARIOUS EMBODIMENTS

In this application, the use of the singular includes the plural unless specifically stated otherwise. In this application, the use of "or" means "and/or" unless stated otherwise. Furthermore, the use of the term "including", as well as other forms, such as "includes" and "includes", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The term "disc" as used herein refers to a multi-layer member to house sample chambers. In various embodiments, the disc can be constructed of any material including, but not limited to, glass, plastic, and/or composite material that is compatible with polymerase chain reaction (PCR). Several such materials are known to one skilled in the art of thermal cycling, including, but not limited to, polymethyl methacylate (PMMA). In various embodiments, the disc can be transparent and/or opaque to visible light. In various embodiments, the disc can be manufactured using a variety of methods known in the art of micro-electro-mechanical systems ("MEMS") including, but not limited to, LIGA, laser-etch, photo-lithography, etc. In various embodiments, the disc can be flat or have a diameter substantially greater than its width. In various embodiments, the disc can have any shape including, but not limited to, circular, triangular, rectangular, star-shaped, etc.

The term "Thermoelectric module" as used herein refers to Peltier devices, also known as thermoelectric coolers (TEC), that are solid-state devices that function as heat pumps. In various embodiments, the Thermoelectric module can comprise two ceramic plates with a bismuth telluride composition between the two plates. In various embodiments, when an electric current can be applied, heat is moved from one side of the device to the other, where it can be removed with a heat sink and/or a thermal diffusivity plate. In various embodiments, the"cold" side can be used to pump heat out of a thermal block assembly. In various embodiments, if the current is reversed, the device can be used to pump heat into the thermal block assembly. In various embodiments, Thermoelectric modules can be stacked to achieve an increase in the cooling and heating effects of heat pumping. Thermoelectric modules are known in the art and manufactured by several companies, including, but not limited to, Tellurex Corporation (Traverse City, Mich.), Marlow Industries (Dallas, Tex.), Melcor (Trenton, N.J.), and Ferrotec America Corporation (Nashua, N.H.).

The term "heating element" as used herein refers to devices that introduce and/or remove heat. This definition can include Thermoelectric modules as they are defined above. Other nonlimiting exemplary heating elements include, but are not limited to, resistive heaters and convective heaters (i.e., forced-air heaters).

The term "thermal cycling" as used herein refers to heating, cooling, temperature ramping up, and/or temperature ramping down. In various embodiments, thermal cycling during temperature ramping up, when heating a disc above ambient temperature (20° C.), can comprise resistive heating and/or pumping heat into the disc by a thermoelectric module as distinguished by diffusion of heat away from the disc. In various embodiments, thermal cycling during temperature ramping down, when cooling the thermal block assembly above ambient temperature (20° C.), can comprise pumping heat out of a disc by the thermoelectric module and diffusion of heat away from the disc.

The term "sample" as used herein includes any reagents, solids, liquids, and/or gases. Exemplary samples may comprise anything capable of being thermally cycled.

The term "turbulence inducing area" as used herein refers to regions that encourage the shearing, mixing, and/or movement of air. Non-limiting examples of turbulence inducing areas include depressions, notches, pegs, slots, vanes, staggered vanes, and/or projections. In various embodiments, the turbulence inducing area can be located on a moving object, such as, for example, a rotating disc. The rotation, then, can cause the turbulence inducing area to generate mixing, shearing, and/or movement of air. In various embodiments, the turbulence inducing area can be located nearby a moving object, such as, for example, on the heat rings which can partially surround a rotating disc.

The term "optical emitter" as used herein refers to a source of irradiance that can provide excitation of a label in the sample. Light sources can include, but are not limited to, white light, halogen lamp, lasers, solid state laser, laser diode, micro-wire laser, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The term "label" refers to any molecule or set of molecules that can provide a detectable signal. In certain embodiments, a label can bind to another moiety or complex that produces a signal or that interacts with another moiety to produce a signal.

Labels also include, but are not limited to, fluorescent molecules, including, but not limited to, fluoresceins, which include, but are not limited to, 6-carboxyfluorescein, 2',4',1, 4,-tetrachlorofluorescein, and 2',4',5',7',1,4-hexachlorofluorescein (see, e.g., U.S. Pat. Nos. 5,188,934; 6,008,379; and 6,020,481); rhodamines (see, e.g., U.S. Pat. Nos. 5,366,860; 5,847,162; 5,936,087; 6,051,719; and 6,191,278); benzophenoxazines (see, e.g., U.S. Pat. No. 6,140,500); energy-transfer fluorescent dyes, which comprise pairs of donors and acceptors (see, e.g., U.S. Pat. Nos. 5,863,727; 5,800,996; and 5,945,526); and cyanines (see, e.g., WO 97/45539); as well as any other fluorescent moiety capable of generating a detectable signal.

Other exemplary labels include, but are not limited to, luminescent molecules and molecules that can be involved in luminescent reactions, such as luciferin-luciferase reactions, as a non-limiting example. Labels also include, but are not limited to, chemiluminescent and electroluminescent molecules and reactions. In certain embodiments, chemiluminescent labels interact with a chemiluminescent substrate to produce a chemiluminescent signal. In certain embodiments, chemiluminescent labels bind to a molecule or complex that interacts with a chemiluminescent substrate to produce a chemiluminescent signal. As a non-limiting example, chemiluminescent labels may be exposed to film. Development of the film indicates whether or not the chemiluminescent labels are present in the sample and/or the quantity of the chemiluminescent labels in the sample.

Other exemplary labels include, but are not limited to, donor-acceptor interactions, in which a donor molecule emits energy that is detected by an acceptor molecule. The acceptor molecule then emits a detectable signal.

In certain embodiments, the term label refers to a molecule that interacts with a second molecule or other member of a set of molecules to provide a detectable signal. The signal may be provided by either the first molecule or the second molecule, e.g., FRET (Fluorescent Resonance Energy Transfer), or set of molecules. Labels include, but are not limited to, light-emitting or light-absorbing compounds which generate or quench a detectable fluorescent, chemiluminescent, or bioluminescent signal (see, e.g., Kricka, L. in Nonisotopic DNA Probe Techniques (1992), Academic Press, San Diego, pp. 3-28).

Labels also include, but are not limited to, quantum dots. "Quantum dots" refer to semiconductor nanocrystalline compounds capable of emitting a second energy in response to exposure to a first energy. Typically, the energy emitted by a single quantum dot always has the same predictable wavelength. Exemplary semiconductor nanocrystalline compounds include, but are not limited to, crystals of CdSe, CdS, and ZnS. Suitable quantum dots according to certain embodiments are described, e.g., in U.S. Pat. Nos. 5,990,479 and 6,207,392 B1, and in "Quantum-dot-tagged microbeads for multiplexed optical coding of biomolecules," Han et al., Nature Biotechnology, 19:631-635 (2001).

Labels of the present invention also include radioisotopes. Radioisotopes may be directly detected, or may excite a fluorophore that emits a wavelength of light that is then detected, e.g., using a scintillation counter.

Other exemplary labels include, but are not limited to, molecules that are involved in infrared photon release.

Other examples of certain exemplary labels include particles with coded information, such as barcodes, and also include the microparticle tags described, e.g., in U.S. Pat. No. 4,053,433. Certain other non-radioactive labeling methods, techniques, and reagents are reviewed in: Non-Radioactive Labeling, A Practical Introduction, Garman, A. J. (1997) Academic Press, San Diego.

Finally, labels may be used according to any one of a large number of known techniques employing known labels, linkages, linking groups, affinity sets, reagents, reaction conditions, and analysis and purification methods.

Figure 1:
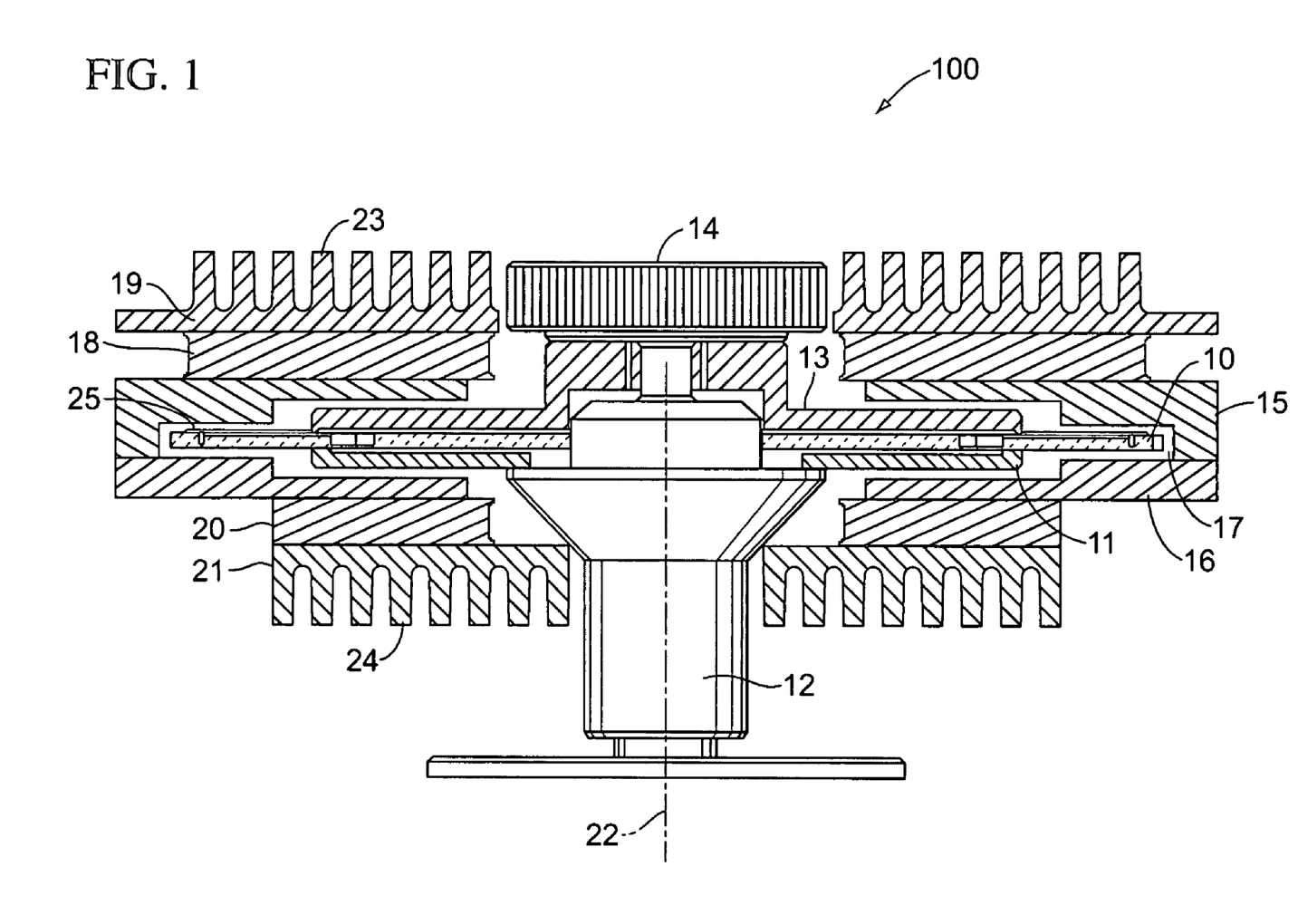
FIG. 1 illustrates a cross-sectional side view of a thermal cycler device according to various embodiments.

According to various embodiments, as illustrated in FIG. 1, a thermal cycler device 100 can include disc 10 that can be positioned on platen 11. Platen 11 can be positioned on spindle 12. According to various embodiments, platen 11 can be attached to spindle 12. According to various embodiments, cap 13 can be attached to lid 110, as is discussed below and shown in FIG. 11. According to various embodiments, cap 13 can be positioned on top of disc 10 and secured with thumbscrew 14. According to various embodiments, spindle 12 can rotate about axis 22 to provide rotation for disc 10, platen 11, cap 13, and thumbscrew 14.

According to various embodiments, device 100 can include upper heat ring 15 and lower heat ring 16 that together can bound air gap 17 within which disc 10 can rotate. In various embodiments, either upper heat ring 15 or lower heat ring 16, or both, can contain one or more resistive heaters (not shown). In various embodiments, each resistive heater (not shown) can transfer heat to either upper heat ring 15 or lower heat ring 16 to provide heat to air gap 17.

According to various embodiments, device 100 can include an upper Thermoelectric module 18 and/or a lower Thermoelectric module 20. Upper Thermoelectric module 18 can contact upper heat ring 15 to provide heat removal. Upper heat sink 19 can contact upper Thermoelectric module 18 to provide heat removal from upper Thermoelectric module 18. Upper heat sink 19 can provide heat radiation into the surrounding air and/or environment to disperse the heat generated at upper heat ring 15 and conducted through upper Thermoelectric module 18 into upper heat sink 19. According to various embodiments, heat sink 19 can include fins 23 to increase surface area and allow for more efficient dissipation of heat. According to various embodiments, a fan (not shown) can provide circulation of the air and increase heat removal from heat sink 19. According to various embodiments, lower Thermoelectric module 20 can contact lower heat ring 16 to provide heat removal from lower heat ring 16. Lower heat sink 21 can contact lower Thermoelectric module 20 to provide heat removal from lower Thermoelectric module 20. Lower heat sink 21 can provide heat radiation into the surrounding air and/or environment to disperse the heat generated at lower heat ring 16 and conducted through lower Thermoelectric module 20 into lower heat sink 21. According to various embodiments, heat sink 21 can include fins 24 to increase surface area and allow for more efficient dissipation of heat. According to various embodiments, a fan (not shown) can provide circulation of the air and increase heat removal from heat sink 21.

Figure 2A:
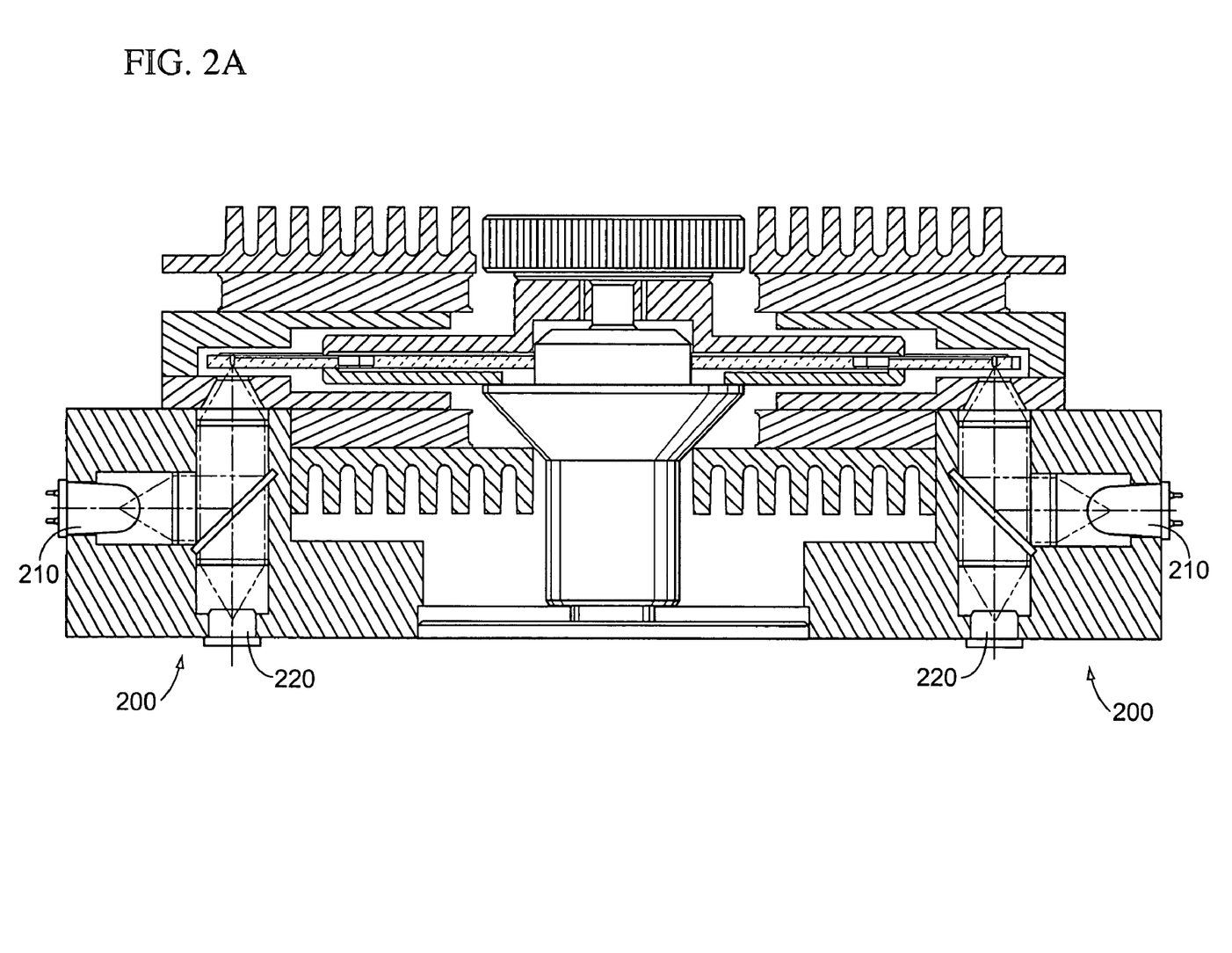
FIG. 2A illustrates a cross-sectional side view of a light detection system with the thermal cycler device illustrated in FIG. 1 according to various embodiments.
Figure 2B:
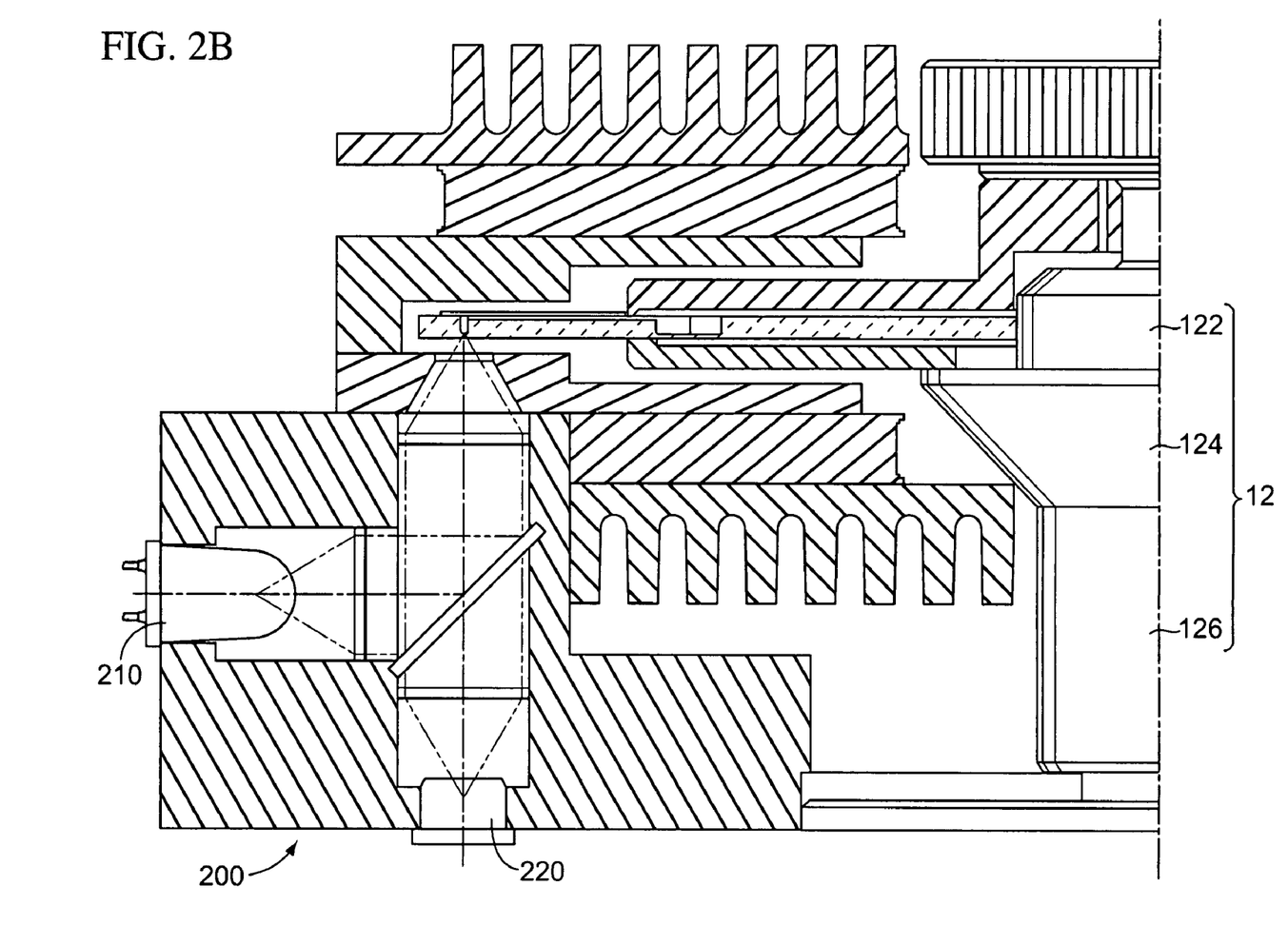
FIG. 2B illustrates a magnified view of FIG. 2A according to various embodiments.
Figure 2C:
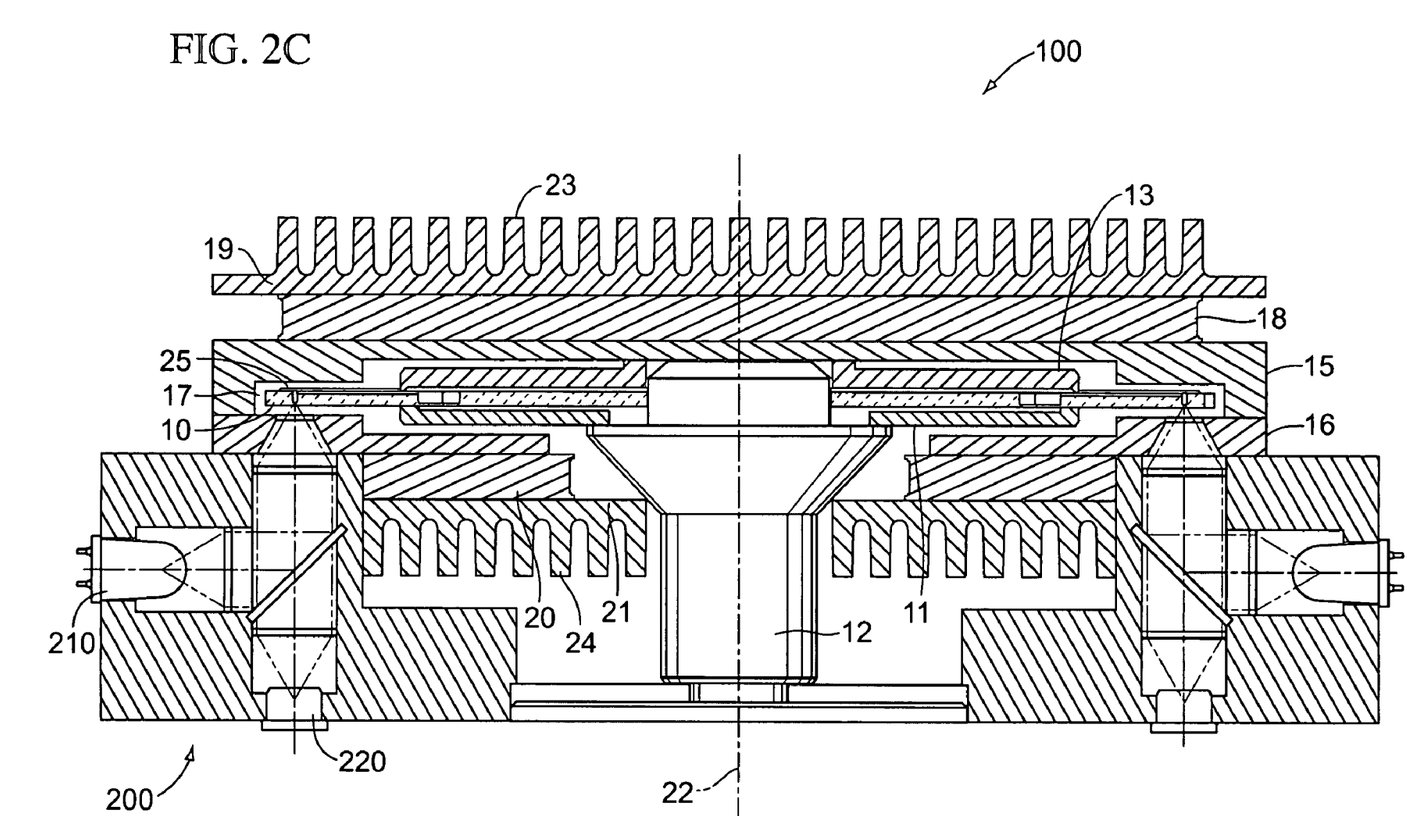
FIG. 2C illustrates a cross-sectional side view of a light detection system with the thermal cycler device illustrated in FIG. 1 according to various embodiments.

According to various embodiments, device 100 can include at least one optics subassembly 200 (See, for example, FIGS. 2A, 2B, and 2C). According to various embodiments, optics subassembly 200 can include excitation optics and detection optics to detect light emitted by at least one label in a sample. In various embodiments, the excitation optics can include at least one optical emitter 210 which emits light of at least one predetermined wavelength that can excite the sample into emitting light of another wavelength. In various embodiments, the detection optics can include at least one detector 220 that can detect the light emitted by the sample. Both excitation and detection optics are known in the art of light detection. In various embodiments, fluorescent light is emitted by a sample.

According to various embodiments, as illustrated in FIG. 2C, device 100 can include upper heat sink 19, upper heat ring 15, and/or upper Thermoelectric module 18 which are continuous throughout. In certain such embodiments, thumbscrew 14 is not used to facilitate the positioning of disc 10 inside device 100. According to various embodiments, other methods of placing disc 10 inside device 100 can include a hinged lid (see, for example, FIG. 11) or a loading tray (see, for example, FIG. 12), as discussed in further detail below.

Figure 3:
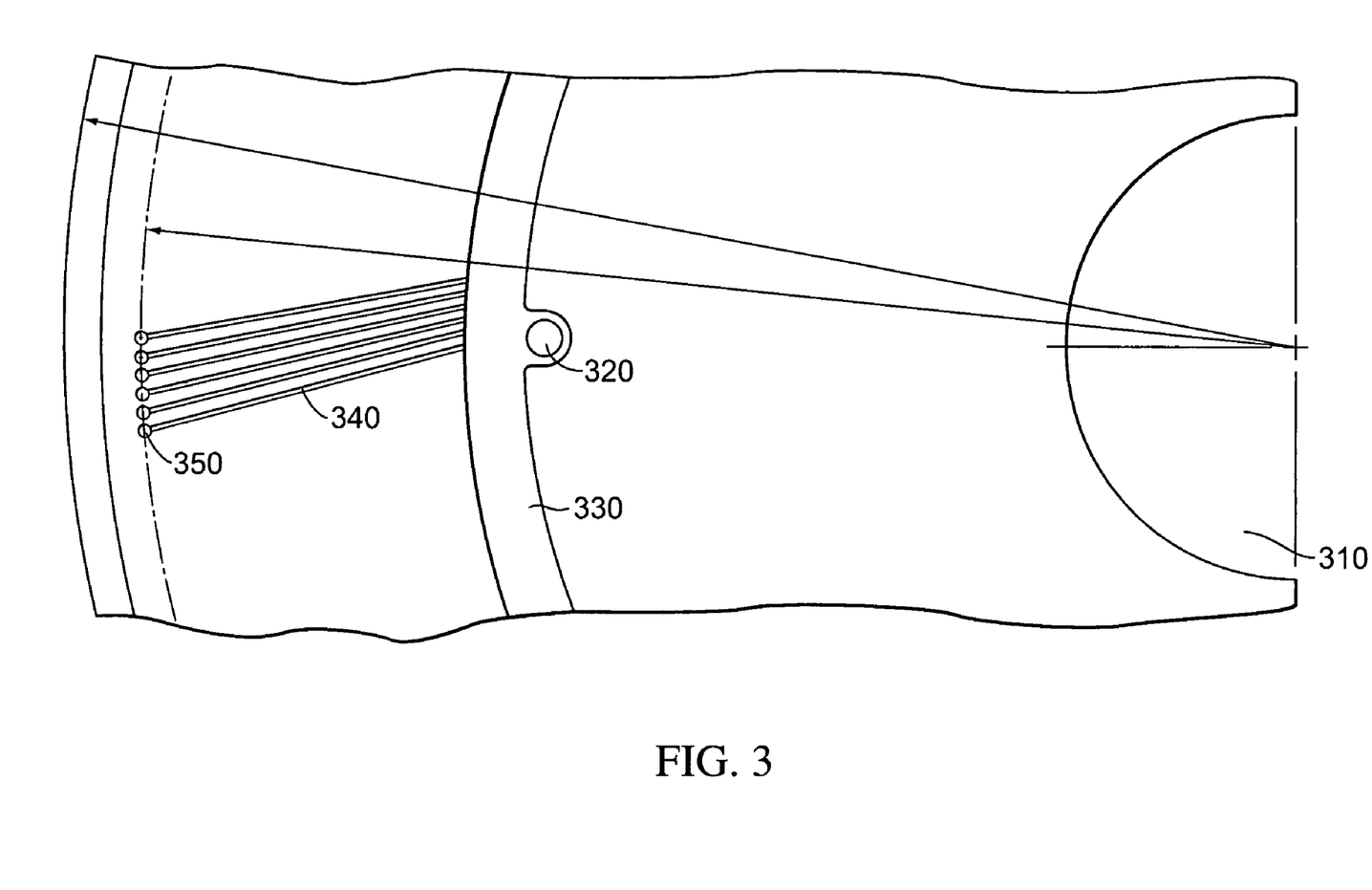
FIG. 3 illustrates a partial top view of a disc according to various embodiments.

According to various embodiments, as illustrated in FIG. 3, disc 10 can include opening 310 at the center of disc 10. As illustrated in FIG. 10, in various embodiments, disc 10 can be circular in shape. As illustrated in FIG. 1, opening 310 can provide alignment and attaching of disc 10 with spindle 12, to provide rotation of disc 10. According to various embodiments, spindle 12 can include hub 122, holder 124 and/or shaft 126, as shown in FIG. 2B. According to various embodiments, platen 11 can attach to holder 124 and/or hub 122 (see, for example, FIGS. 2B and 2C). In various embodiments, disc 10 can attach to platen 11. According to various embodiments, disc 10 can attach to holder 124 and/or hub 122. According to various embodiments, disc 10 can include film 25 to act as a sealant, as shown, for example, in FIGS. 1 and 9.

According to various embodiments, disc 10 can include at least one loading port 320 for access to the interior of disc 10. See, for example, FIG. 3. According to various embodiments, a sample can be provided to disc 10 via loading port 320. According to various embodiments, loading port 320 can connect to at least one distribution ring 330 that can store the sample (not shown) introduced through loading port 320. See, for example, FIG. 3. In various embodiments, at least one channel 340 can route the sample (not shown) from distribution ring 330 to at least one sample chamber 350. See, for example, FIG. 3. According to various embodiments, the sample can be routed during loading. According to various embodiments, the sample can be routed after loading. According to various embodiments, the sample can be routed by rotation of disc 10. In various embodiments, rotation of disc 10 can provide a centrifugal force to route the sample (not shown) from distribution ring 330 to sample chamber 350. According to various embodiments, many configurations of the number and position of sample chambers 350 may be employed as understood by one skilled in the art of microfluidics and/or assay design.

Figure 4A:
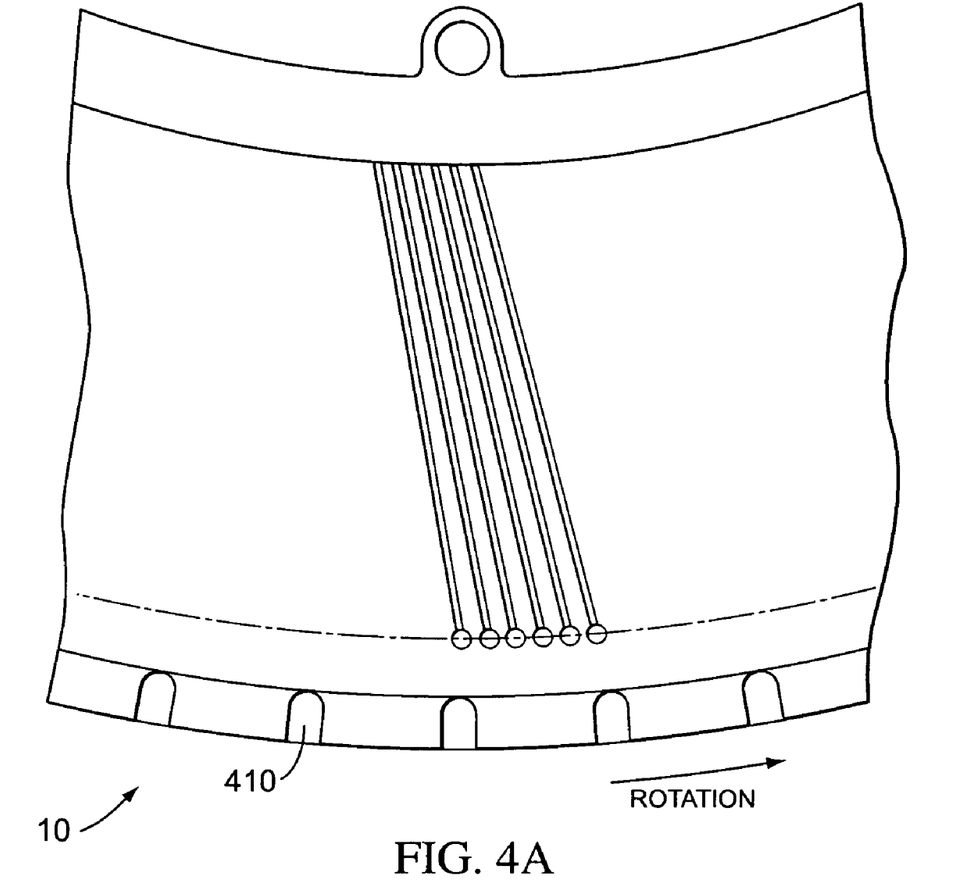
FIG. 4A illustrates a partial top view of a disc including peripheral slots according to various embodiments.
Figure 4B:
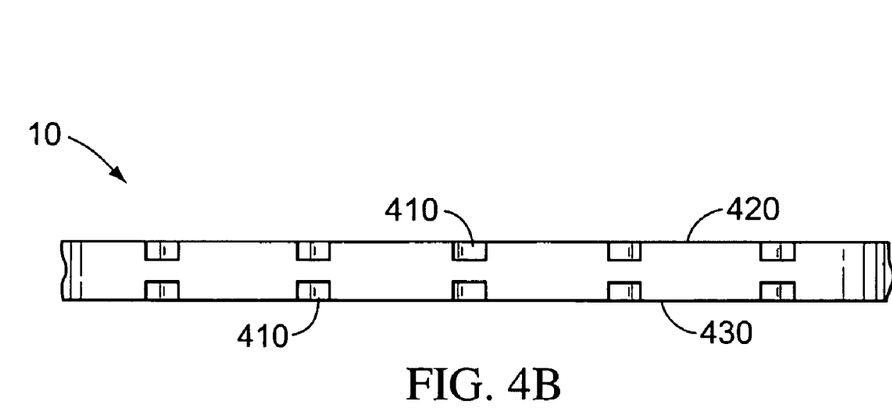
FIG. 4B illustrates a partial side view of a disc including peripheral slots according to various embodiments.

According to various embodiments, disc 10 can include one or more slots 410 as shown in FIGS. 4A and 4B. In various embodiments, slots can be cast, forged, molded, and/or machined. In various embodiments, slots can be included in a separate component that can be configured as a circumferential attachment to a disc (not shown). Although FIGS. 4A and 4B show slots 410 separated from each other by approximately equal distances, other arrangements can be used in various embodiments. In various embodiments, slots 410 may be in the form of indentations that recede from either top surface 420 or bottom surface 430 of disc 10, or both. In various embodiments, although FIGS. 4A and 4B show separate slots on the top surface 420 of disc 10 from slots 410 on the bottom surface 430 of disc 10, in various embodiments slots may also extend through the thickness of a disc. FIGS. 4A and 4B show slots 410 positioned on the circumference of disc 10. However, in various embodiments, slots can be formed more toward the center of a disc. Indeed, in various embodiments, slots can be formed both on the circumference and at locations more toward the center of a disc.

Figure 5A:
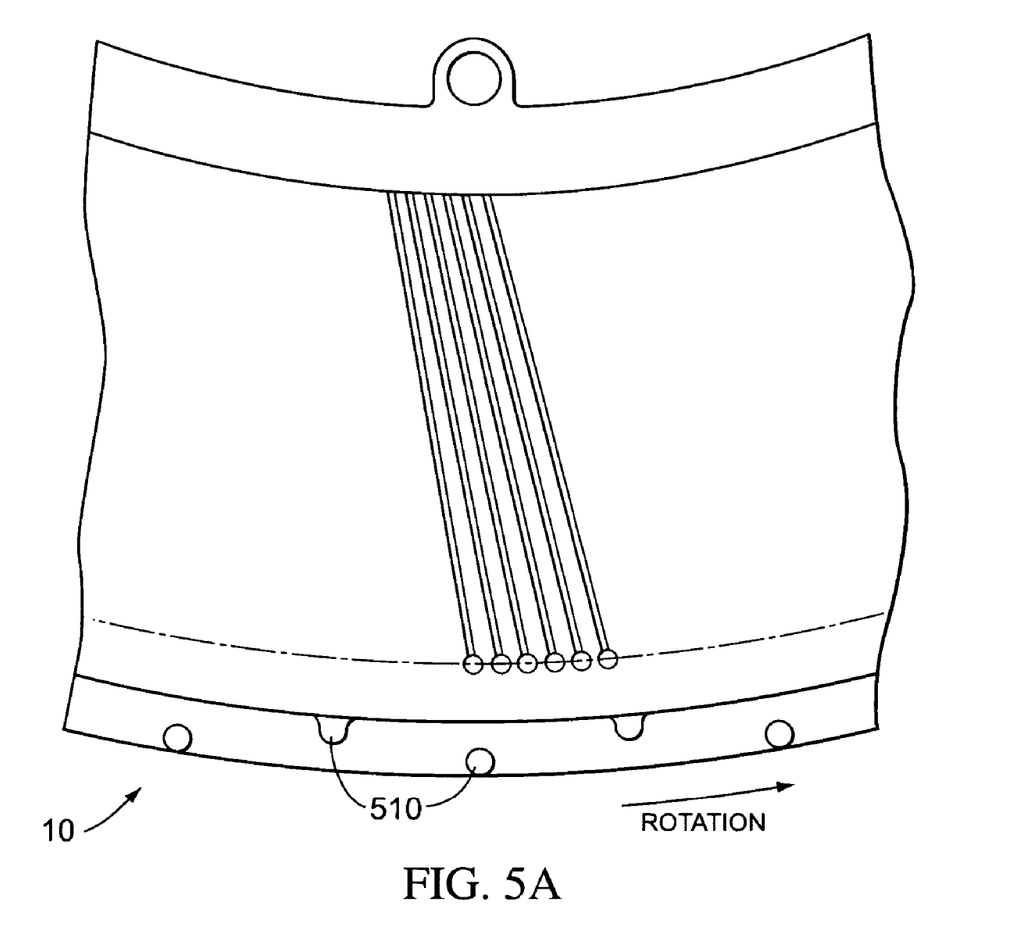
FIG. 5A illustrates a partial top view of a disc including staggered pegs according to various embodiments.
Figure 5B:
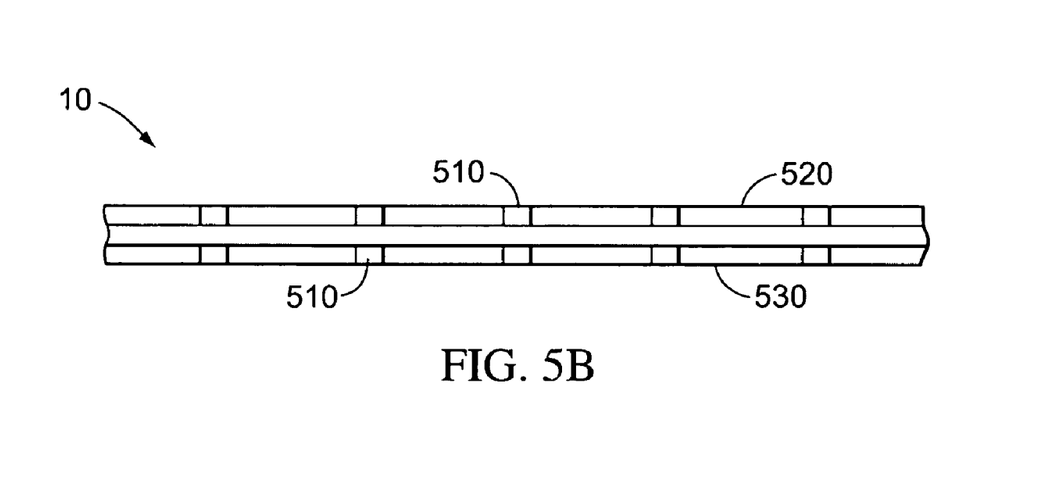
FIG. 5B illustrates a partial side view of a disc including staggered pegs according to various embodiments.
Figure 6A:
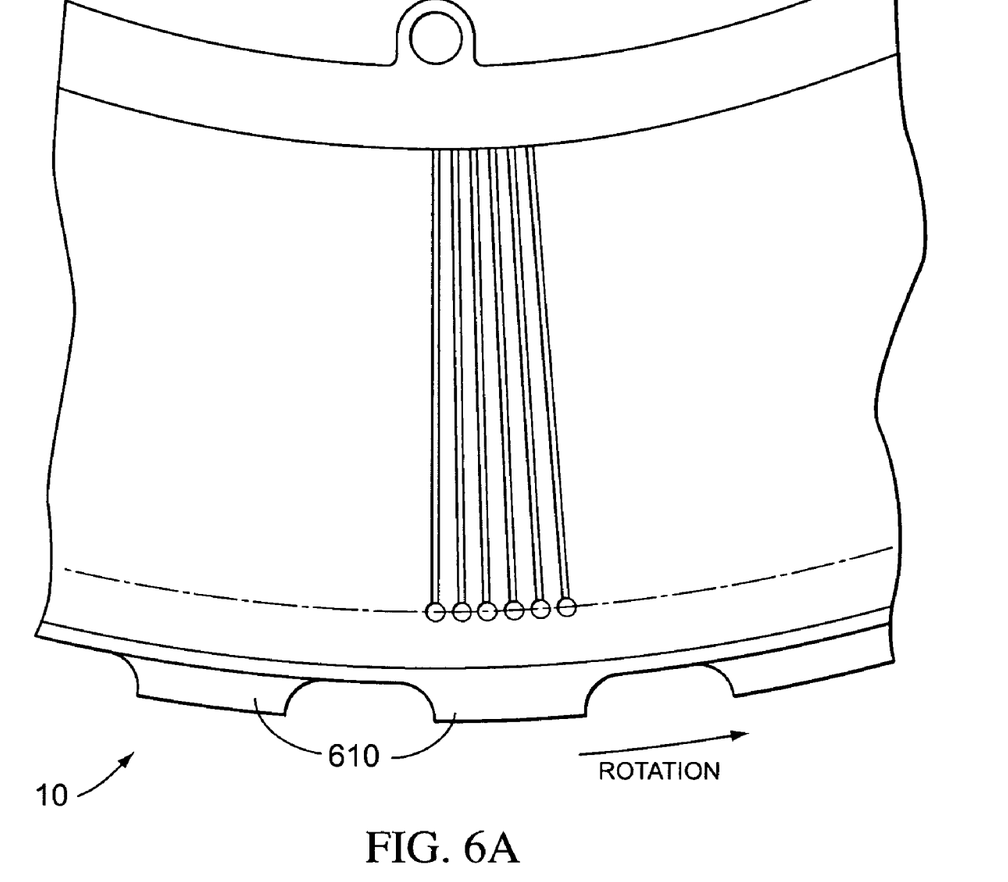
FIG. 6A illustrates a partial top view of a disc including staggered vanes according to various embodiments.
Figure 6B:
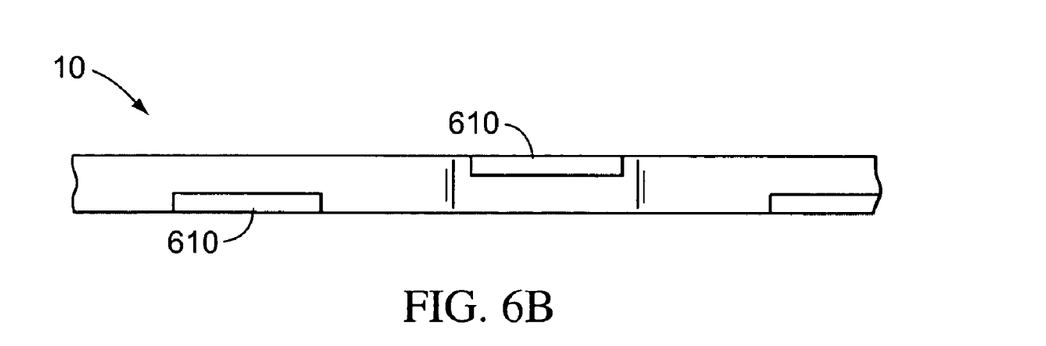
FIG. 6B illustrates a partial side view of a disc including staggered vanes according to various embodiments.
Figure 7A:
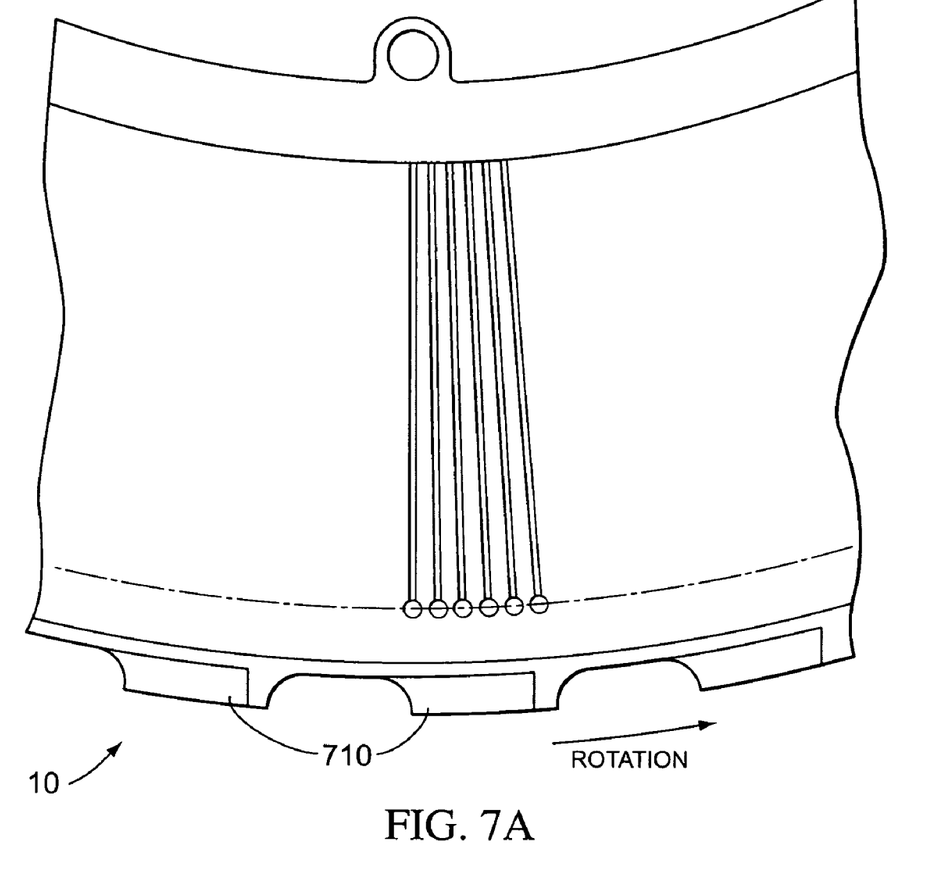
FIG. 7A illustrates a partial top view of a disc including angled vanes according to various embodiments.
Figure 7B:
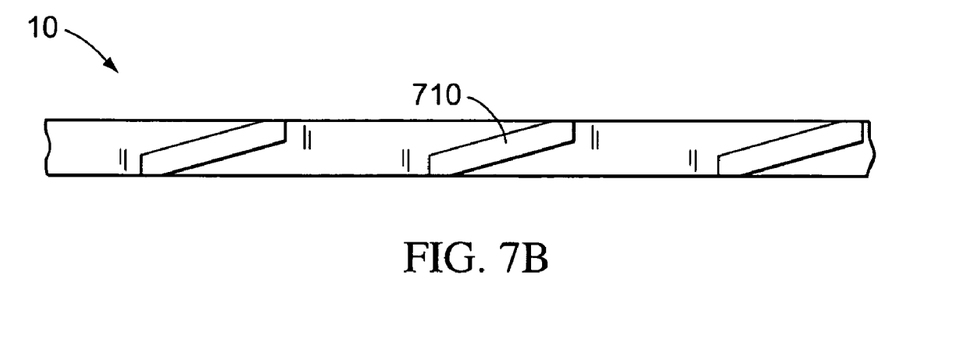
FIG. 7B illustrates a partial side view of a disc including angled vanes according to various embodiments.

According to various embodiments, disc 10 can include one or more pegs 510 as shown, for example, in FIGS. 5A and 5B. According to various embodiments, disc 10 can include one or more vanes 610 as shown, for example, in FIGS. 6A and 6B. According to various embodiments, disc 10 can include one or more staggered vanes 710 as shown, for example, in FIGS. 7A and 7B.

Figure 8A:
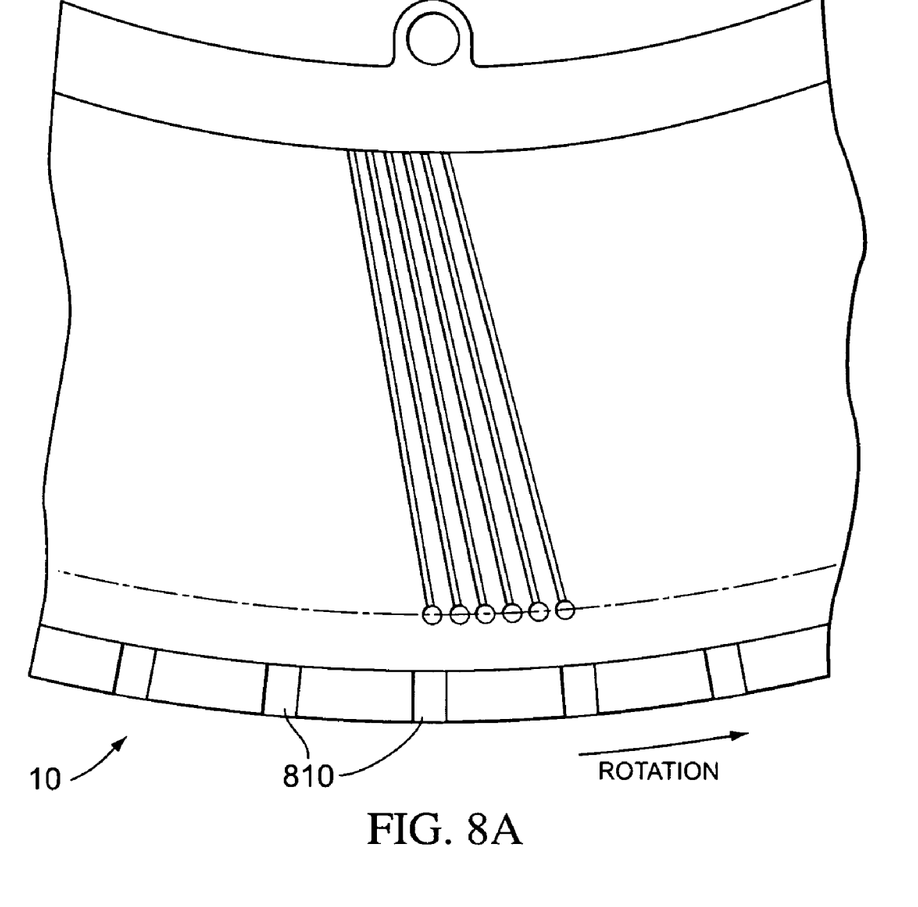
FIG. 8A illustrates a partial top view of a disc including projections according to various embodiments.
Figure 8B:
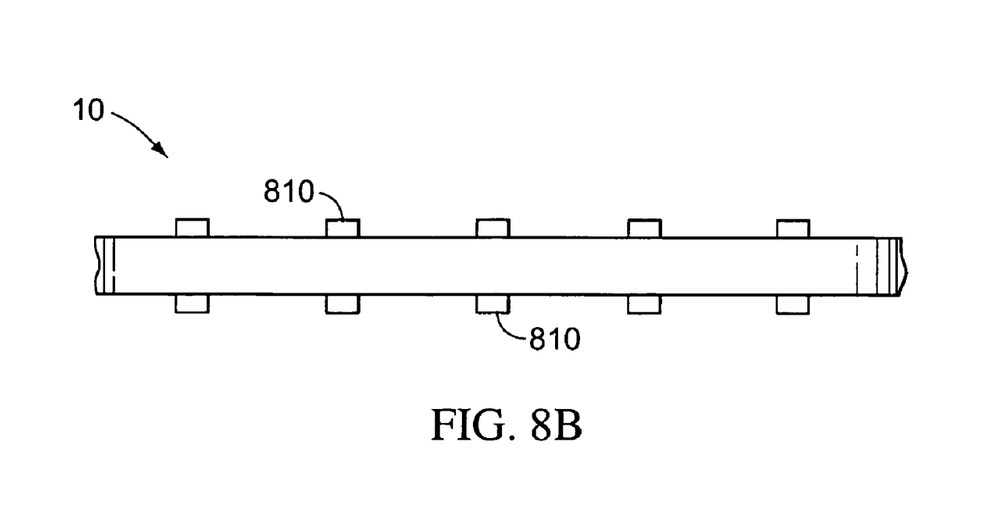
FIG. 8B illustrates a partial side view of a disc including projections according to various embodiments.

According to various embodiments, disc 10 can include one or more projections 810 as shown, for example, in FIGS. 8A and 8B. In various embodiments, projections can be machined, cast, and/or forged. In various embodiments, projections 810 can be attached to disc 10. An exemplary non-limiting attachment may include, but is not limited to, use of an adhesive, magnet, and/or mechanical fastening. In various embodiments, both slots and projections can be included on a disc. Although FIGS. 8A and 8B show projections 810 separated from each other by approximately equal distances, other arrangements can be used in various embodiments. In various embodiments, projections 810 may extend from either top surface 820 or bottom surface 830 of disc 10, or both. In various embodiments, projections can be included in a separate component that can be configured as a circumferential attachment to a disc (not shown).

According to various embodiments, a disc can include any combination of slots, pegs, vanes, staggered vanes, and/or projections.

Figure 9:
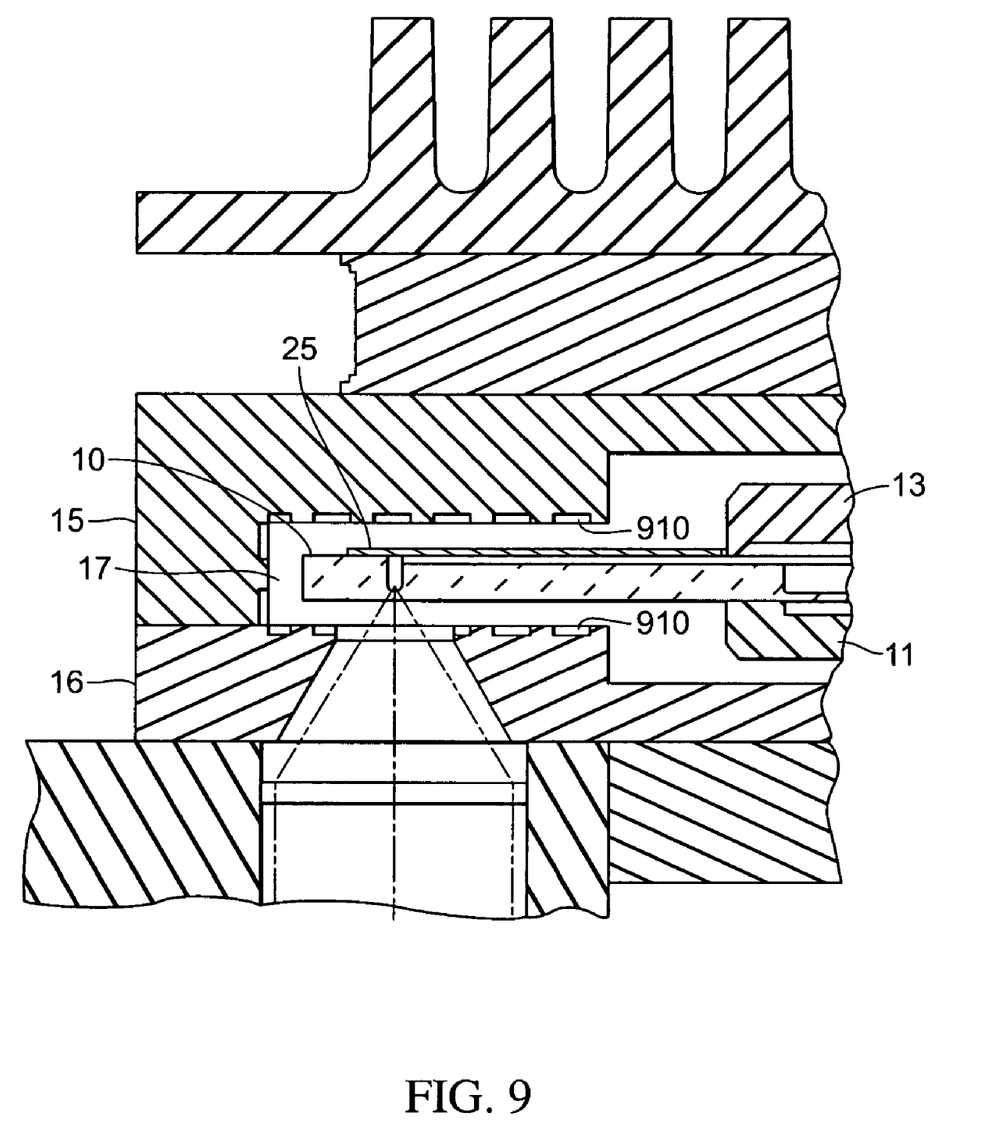
FIG. 9 illustrates a partial cross-sectional view of a light detection system with a thermal cycler device including grooves on upper and lower heat rings according to various embodiments.
Figure 10:
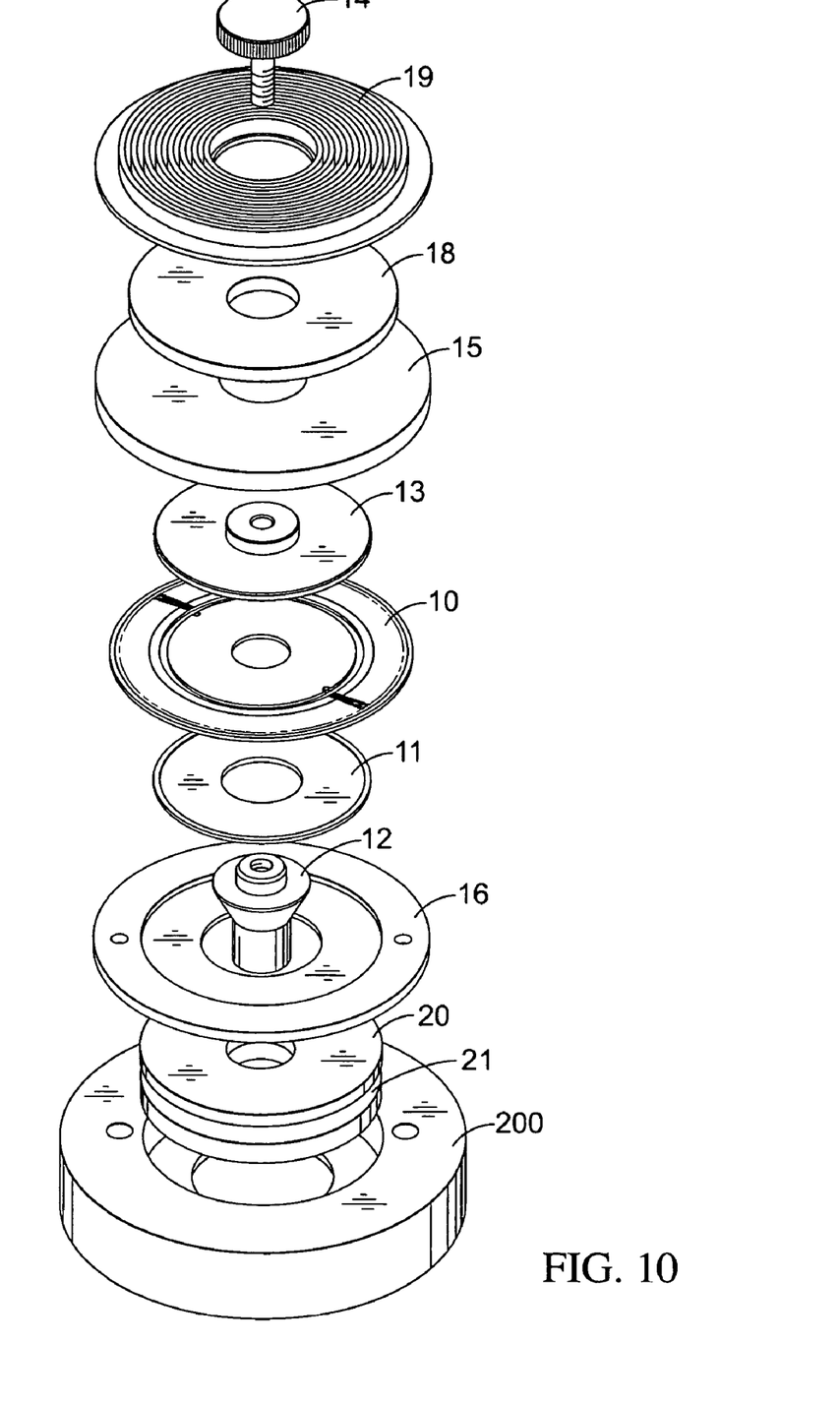
FIG. 10 illustrates a perspective exploded view of a light detection system with the thermal cycler device according to various embodiments.

According to various embodiments, upper heat ring 15 and/or lower heat ring 16 can include slots 910 and/or projections (not shown), as shown, for example, in FIG. 9. In various embodiments, both upper heat ring and/or lower heat ring and a disc can include slots and/or projections. In various embodiments, slots 910 can be replaced with pegs, vanes, staggered vanes and/or projections similar to those discussed above for a disc. In various embodiments, upper heat ring and/or lower heat ring can include slots and/or projections and a disc can include slots, pegs, vanes, staggered vanes, and/or projections. In various embodiments, slots and/or projections can be machined, cast, forged, adhered, magnetized, and/or mechanically fastened to upper heat ring and/or lower heat ring.

Figure 11:
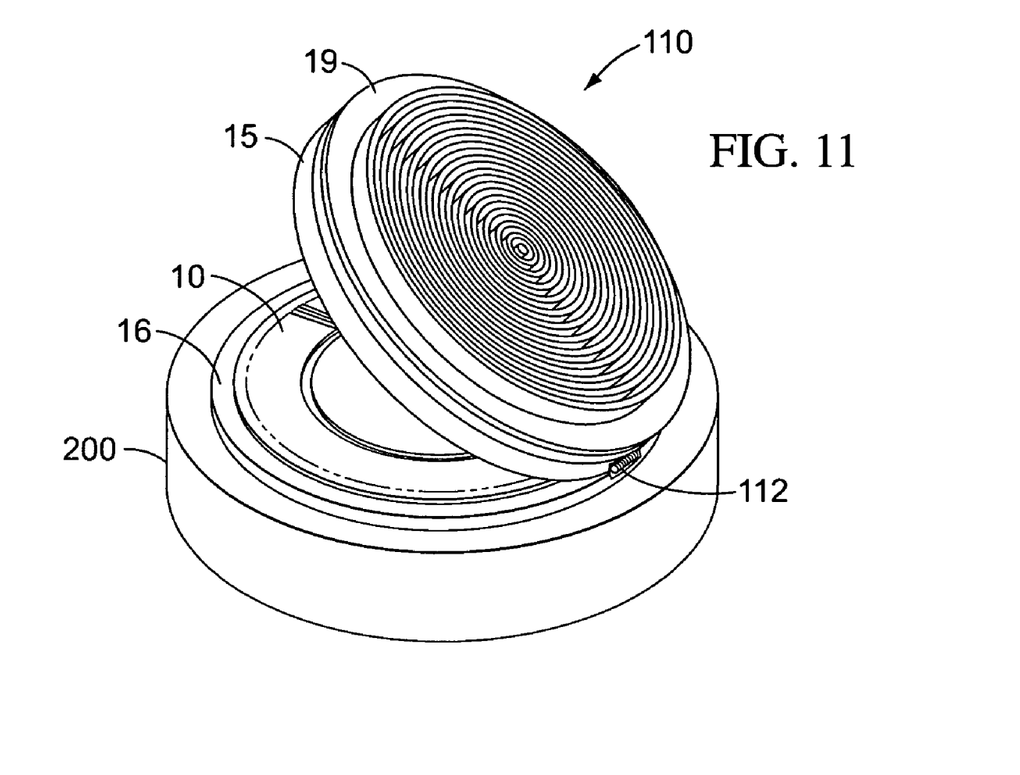
FIG. 11 illustrates a perspective view of a thermal cycler device including a lid according to various embodiments.

According to various embodiments, as illustrated in FIG. 11, device 100 can include lid 110, that can include at least one hinge 112. According to various embodiments, a lid can be hinged between upper heat ring 15 and lower heat ring 16 (FIG. 2C). Thus, in various embodiments, a lid can include upper heat sink 19, upper Thermoelectric device 18, upper heat ring 15 and/or cap 13. In various embodiments, hinge 112 can facilitate access to the inside of device 100, to allow the user to place disc 10 in a position to be rotated by spindle 12 (see, for example, FIGS. 2A through 2C). According to various embodiments, lid 110 can be attached to the bottom portion of device 100 by clamps, mechanical interference, adhesives, and/or any other similar fixation method.

Figure 12:
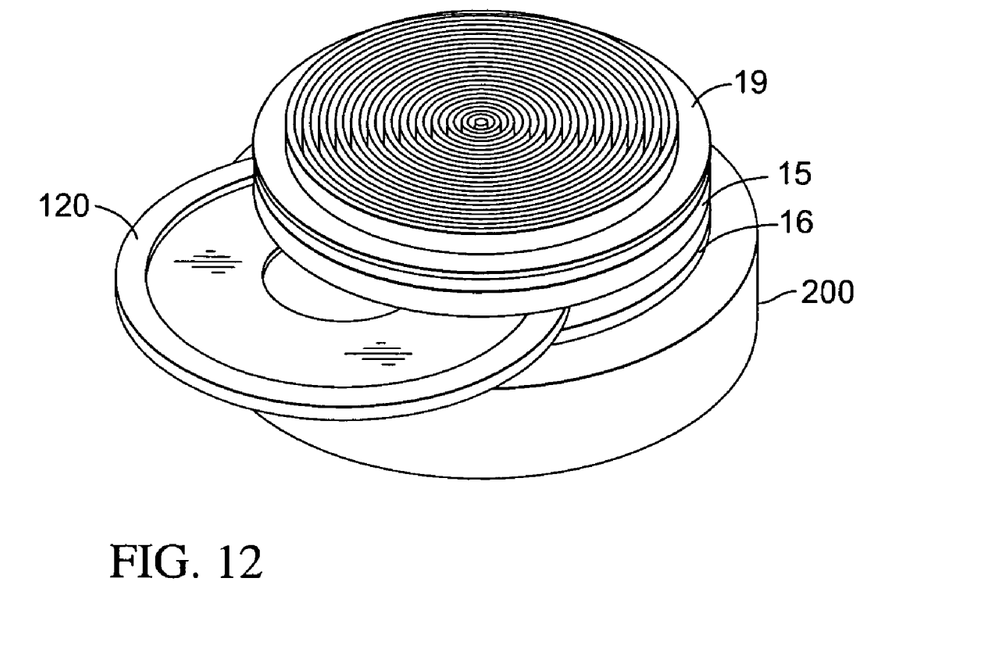
FIG. 12 illustrates a perspective view of a thermal cycler device including a loading tray according to various embodiments.

According to various embodiments, as illustrated in FIG. 12, device 100 can include loading tray 120, which can facilitate placement of disc 10 inside device 100. According to various embodiments, loading tray 120 can be located approximately at the location of platen 11 (see FIG. 2C). In various embodiments, loading tray 120 can replace platen 11. In various embodiments, loading tray 120 can convey and/or align disc 10 upon platen 11. According to various embodiments, loading tray 120 can move in a generally horizontal manner from within device 100 to outside of device 100, in a position that can allow the user to place disc 10 upon loading tray 120. In various embodiments, loading tray 120 can be driven by an electric motor or the like, or can be fully manual, in which case the user can provide movement of loading tray 120. According to various embodiments, after the user places disc 10 upon loading tray 120, loading tray 120 can move to a position within device 100 and can position disc 10 to facilitate rotation of disc 10 by spindle 12. According to various embodiments, spindle 12 can rotate disc 10 by engaging and rotating loading tray 120. According to various embodiments, spindle 12 can move vertically to engage loading tray 120 and/or disc 10 to enable spindle 12 to rotate disc 10 within device 100.

According to various embodiments, when disc is rotated by spindle, each slot and/or projection can contribute to the generation of turbulent airflow and/or shearing of the airflow around disc. In various embodiments, the generation of turbulent airflow around rotating disc 10 can provide convective heat transfer between upper and/or lower heat rings and disc, increasing the transfer of heat. In addition, in various embodiments, rotating disc can eventually reach the mean temperature of the air in air gap, maintaining temperature uniformity of the reactions in each sample chamber despite any non-uniformities of temperature that exist in either or both the upper and lower heat rings.

According to various embodiments, device can include at least one feedback system (not shown). In various embodiments, a feedback system can include thermal sensors (not shown) to detect the temperature of various areas of device, for example sample chambers and/or air gap. In various embodiments, the feedback system can receive information from the thermal sensors and can direct Thermoelectric modules and/or heat rings to produce and/or remove heat.

Example 1: an device 100 can be constructed using a disc 10 that can be about 80 mm in diameter, and about 1.2 mm thick. As is partially shown, for example, in FIG. 3, disc 10 can include a film 25 that can be about 0.1 mm thick. Disc 10 can contain two reagent loading ports 320, one distribution ring 330 and 384 channels 340 that connect to 384 sample chambers 350, located near the periphery of disc 10. Spindle 12 can rotate at about 7000 revolutions per minute, causing a sample to be routed from distribution ring 330 to sample chambers 350 by centrifugal force. Air gap 17 can exist on three sides of disc 10 and can be about 0.8 mm thick. Slots 410/910, pegs 510, and vanes 610, can recede from the surface of a disc or the surface of the upper and/or lower heat rings a distance of about 0.4 mm. Similarly, projections 810 can protrude from the surface of a disc or the surface of the upper and/or lower heat rings a distance of about 0.4 mm.

What is claimed is:

1. A method of thermally cycling, comprising:
   at least one of introducing and removing heat with a heating element;
   rotating a disc to induce a turbulent airflow; and
   positioning the disc in a device for thermal cycling comprising loading a tray to provide access to the interior of the device for thermal cycling,
   wherein the disc is configured to receive samples; and
   wherein there is an air gap between the disc and the heating element.

2. The method of claim 1, further comprising a mechanism configured to rotate the disc.

3. The method of claim 2, wherein the turbulent airflow is induced by a turbulence inducing area on the disc.

4. The method of claim 3, wherein the turbulence inducing area includes at least one of slots, pegs, vanes, staggered vanes, and projections.

5. The method of claim 2, wherein the turbulent airflow is induced by a turbulence inducing area on the heating element.

6. The method of claim 5, wherein the turbulence inducing area includes at least one of slots, pegs, vanes, staggered vanes, and projections.

7. The method of claim 2, further comprising excitation optics and detection optics to detect fluorescent light emitted by at least one label in the sample.

8. The method of claim 2, further comprising a feedback system to control the heating element and provide for substantially uniform heat distribution to at least one sample chamber located on the disc.

9. The method of thermally cycling according to claim 1, further comprising providing substantial thermal uniformity to at least one sample chamber located on the disc.

10. The method of thermally cycling according to claim 1, further comprising exciting a label in at least one sample chamber located on the disc.

11. The method of thermally cycling according to claim 1, further comprising detecting light from the label.

12. The method of thermally cycling according to claim 1, providing access comprises lifting a lid.

* * * * *